US00PP25917P3

(12) United States Plant Patent
Keogh

(10) Patent No.: US PP25,917 P3
(45) Date of Patent: Sep. 22, 2015

(54) **VARIETY OF *TIBOUCHINA* NAMED 'PEACE BABY'**

(50) Latin Name: *Tibouchina×hybrida*
Varietal Denomination: Peace Baby

(71) Applicant: Terry Keogh, Victoria Point (AU)

(72) Inventor: Terry Keogh, Victoria Point (AU)

( * ) Notice: Subject to any disclaimer, the term of this patent is extended or adjusted under 35 U.S.C. 154(b) by 178 days.

(21) Appl. No.: 13/815,677

(22) Filed: Mar. 14, 2013

(65) Prior Publication Data

US 2014/0283243 P1 Sep. 18, 2014

(51) Int. Cl.
*A01H 5/02* (2006.01)

(52) U.S. Cl.
USPC ..... Plt./226
CPC ..... *A01H 5/02* (2013.01)

(58) Field of Classification Search
USPC ..... Plt./226, 263.1
See application file for complete search history.

*Primary Examiner* — Anne Grunberg
(74) *Attorney, Agent, or Firm* — The Webb Law Firm

(57) ABSTRACT

'Peace Baby' is a new variety of *Tibouchina* plant that is suitable for planting in gardens, containers, and in landscaping having tolerance to low temperatures and bright red buds turning into white flowers.

2 Drawing Sheets

Botanical classification: *Tibouchina×hybrida.*
Varietal denomination: 'PEACE BABY'.

BACKGROUND OF THE NEW PLANT

The present invention comprises a new and distinct cultivar of *Tibouchina* plant, botanically known as *Tibouchina×hybrida* and hereinafter referred to by the cultivar name 'Peace Baby'.

The new and ornamental variety was selected by the breeder as a result of an ongoing breeding program that has been conducted by the inventor for more than thirty years at the inventor's nursery in Victoria Point, Queensland, Australia. The purpose of the breeding program is to produce novel varieties of *Tibouchina* in varying plant sizes, flower colors, and which are well-suited to a range of climate zones. 'Peace Baby' is a hybrid plant derived from the deliberate controlled cross-pollination of the unpatented female parent, an individual plant of *Tibouchina organensis*, named 'Totally Moonstruck', and the unpatented male parent, an individual plant of *Tibouchina mutabilis* name 'Jazzie'. The inventor emasculated flowers of the female parent and applied pollen that was freshly collected from the male parent in 2002. The parent plants were isolated to prevent open pollination. In 2005, the inventor selected 'Peace Baby' as a seedling that had been raised from the cross-pollination described herein. Selection was based on the criteria of habit, flower color, plant dimensions, and cold temperature tolerance. The plant was then propagated in 2007 via vegetative cuttings to produce a new generation for final evaluation.

Further, asexual reproductions of 'Peace Baby' in Victoria Point, Queensland, Australia has demonstrated that the combination of characteristics as herein disclosed for the new cultivar are retained and reproduced true to type through more than six successive generations of asexual reproduction.

The color references made herein are to The R.H.S. Colour Chart of The Royal Horticulture Society of London, except where general color terms of ordinary significance are used.

The present invention has not been evaluated under all possible environmental conditions. The phenotype may vary with variation in environment without a change in the genotype of the plant.

The following traits have been repeatedly observed and determined to basic characteristics of 'Peace Baby' which, in combination, distinguish this *Tibouchina* plant as a new and distinct cultivar:

1. Compact size and with rounded plant growth (dwarf form);
2. Mid-sized white flowers;
3. Dense plant habit;
4. Bright red buds;
5. Moderate to fast vigor;
5. Low temperature tolerance; and
6. Woody, long-lived shrub.

The new variety differs from 'Totally Moonstruck' in that 'Peace Baby' has a more consistent flower color, smaller plant size at maturity, and better cold tolerance. 'Peace Baby' differs from its pollen parent in flower color and shorter plant dimensions at maturity.

Further, the new variety does not exhibit a differing margin color, while 'Cool Baby' does (U.S. plant patent application Ser. No. 13/815,690). 'Cool Baby also has smaller mature plant dimensions, a slower growth rate, and darker green leaves than 'Peace Baby'.

BRIEF DESCRIPTION OF THE DRAWINGS

The accompanying photographic drawings illustrate the new variety, with the colors being as nearly true as is possible with color illustrations of this type.

PROPAGATION

Figure 1:
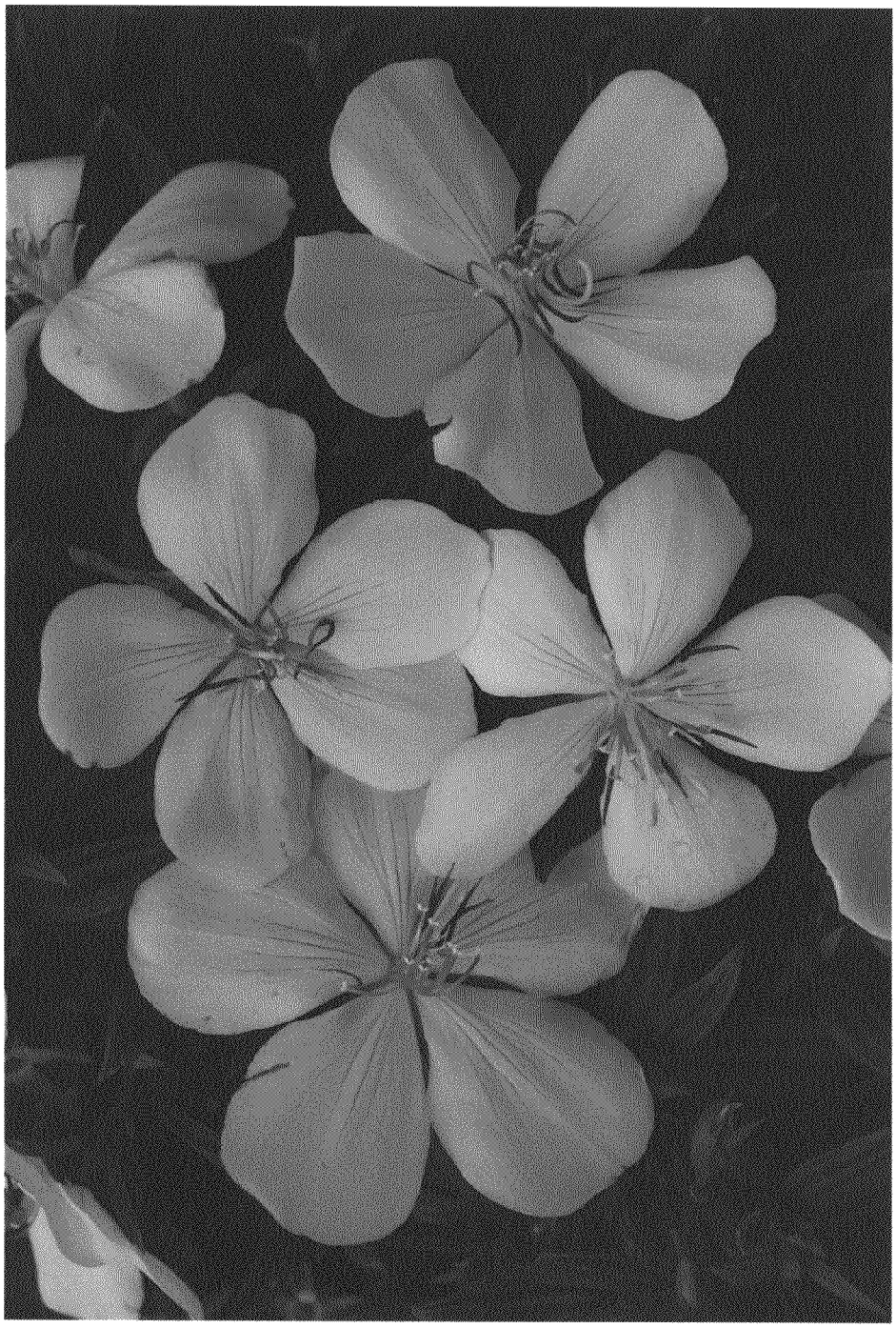
FIG. 1 is close-up photograph of the flowers of the new variety.
Figure 2:
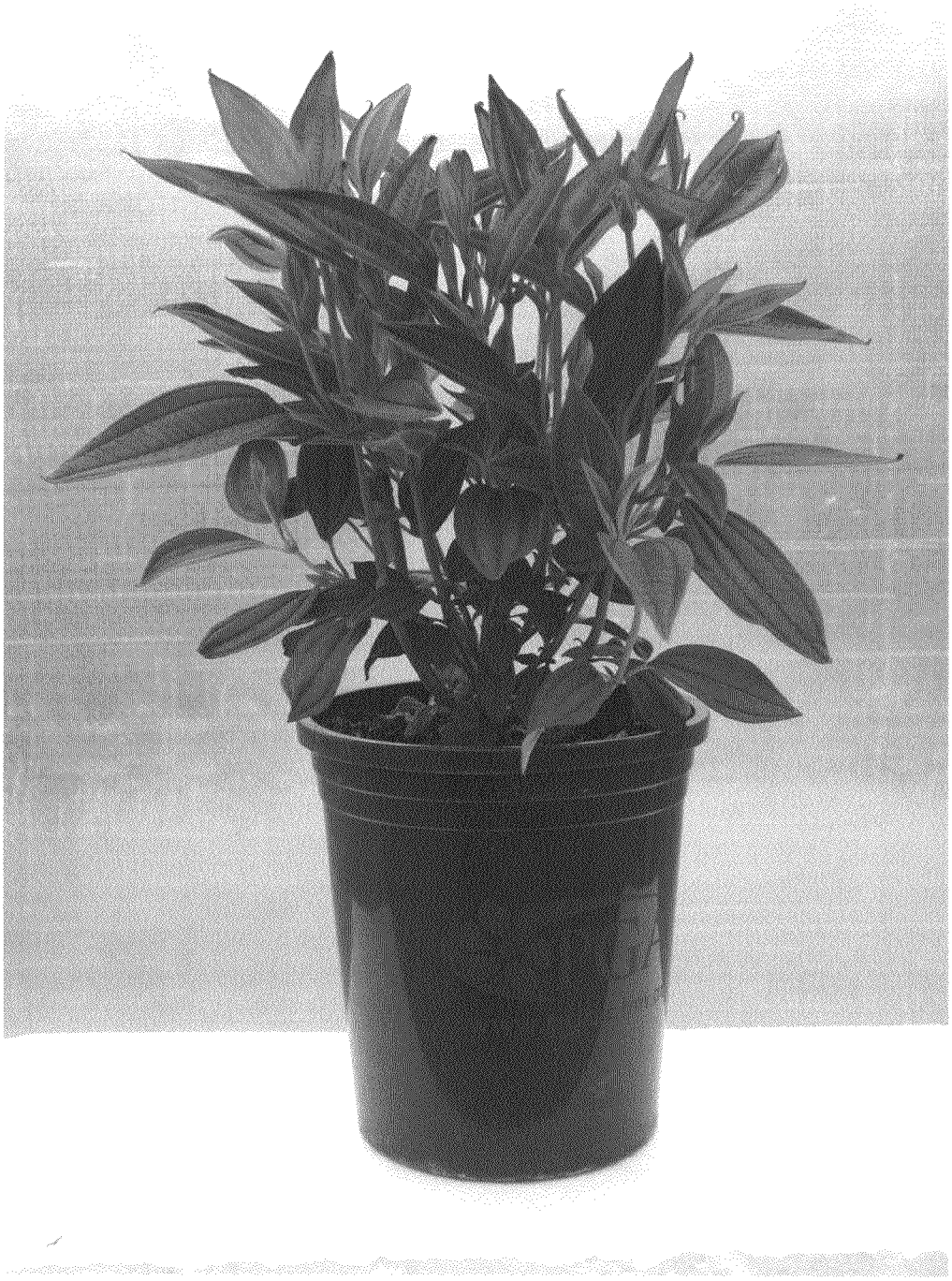
FIG. 2 is a photograph of an entire plant of the new variety

Time to initiate roots: About 14-18 days at approximately 21° C.

Time to produce a rooted cutting: About 25-30 days at 21° C.

PLANT

Plant spread: Approximately 24 cm.
Plant height: 21 cm.
Growth rate: Moderate to fast.
Temperature tolerance: USDA Hardiness Zone 9.
Lateral branches:
*Length.*—Approximately 17.5 cm.
*Diameter.*—Approximately 0.3 cm.
*Quantity.*—About 22.
Age of plant when described: Approximately 14 weeks from a rooted cutting.
Growth habit: Compact; rounded.
Cold tolerance: Medium to strong.
Height at maturity: 1 m.
Width at maturity: 1 m.
Stem:
*Branching habit.*—Strong, basal branching.
*Main stem diameter.*—0.35 cm.
*Lateral stem length* (*average*).—7 cm.
*Lateral stem width* (*average*).—0.17 cm.
*Internode length* (*range*).—2.2 cm to 7.5 cm.
*Shape.*—Square in cross section.
*Surface.*—Rough.
*Branch color.*—Juvenile: 146D. Semi-ripe: 146B. Mature: 199B.
Foliage:
*Leaf.*—Arrangement: Opposite. Division: Simple. Margin: Entire. Shape: Ovate. Base: Cuneate to obtuse. Apex: Acute. Surface (adaxial): Pubescent. Surface (abaxial): Pubescent. Texture (adaxial surface): Prominently ribbed. Texture (abaxial surface): Prominently ribbed. Attachment: Petiolate. Length (range excluding petiole): 3.5 cm to 9 cm. Width (range excluding petiole): 2 cm to 3.8 cm. Color (adaxial surface): 147A and at the margin. Color (abaxial surface): 146B. Color of margin of juvenile foliage not fully expanded: 184A.
*Foliar fragrance.*—None observed to date.
*Venation.*—Pattern: Reticulate; 3 primary parallel veins. Color (adaxial surface): 147B. Color (abaxial surface): 146D. Prominence (adaxial surface): Depressed. Vein prominence (abaxial surface): Raised.
*Petiole.*—Length (range): 1.3 cm to 2.2 cm. Color: 184A and 178B. Surface: Pubescent. Shape: Cylindrical, but flattened on the adaxial surface.
Flower:
*Shape.*—Rotate.
*Aspect.*—Facing upward and outward.
*Inflorescence type.*—Solitary.
*Persistent or self-cleaning.*—Self-cleaning.
*Blooming period.*—Summer through fall; can bloom sporadically during other times.
*Inflorescence fragrance.*—None observed to date.
*Petals.*—Number: 5. Margin: Entire. Apex: Obtuse. Base: Broadly attenuate. Shape: Obovate. Surface (abaxial and adaxial): Glabrous. Color (of both surfaces): NN155A. Fused or unfused: Unfused.
*Buds.*—Shape: Elliptic. Color: 181A. Surface: Pubescent. Apex: Acute.
*Calyx.*—Shape: Cupule. Color: Ranges between 181A and 44A as bud develops and flower opens.
*Sepals.*—Quantity: 5 in number. Surface (adaxial): Smooth. Surface (abaxial): Puberulent and hair color is 197D. Color (adaxial surface): Ranges between 181A and 144D. Color (abaxial surface): 181A. Margin: Entire. Apex: Acute. Base: Truncate. Fused or unfused: Unfused.
*Peduncle.*—Dimensions: 1 m in length and 2 m in diameter. Shape: Cylindrical. Surface: Pubescent.
Reproductive organs:
*Stamens.*—Number: 10. Color: 84B. Length: 2 cm. Width: 1 mm.
*Anthers.*—Color: Ranges between N89A and 155A. Shape: Sickle.
*Pollen.*—None observed.
*Pistil.*—Number: 1. Shape: Columnar.
*Stigma.*—Shape: Flattened.
*Ovary.*—Color: N44A. Shape: Cupule. Surface: Pubescent. Position: Inferior.
*Seeds.*—No seeds have been observed to date.

I claim:

1. A new and distinct variety of *Tibouchina* plant named 'Peace Baby' as herein described and illustrated.

* * * * *